United States Patent
Viöl et al.

(10) Patent No.: US 7,330,755 B2
(45) Date of Patent: Feb. 12, 2008

(54) APPARATUS FOR PREPARING A FINGER NAIL OR A TOE NAIL FOR A COATING

(75) Inventors: Wolfgang Viöl, Heldeweg 11, D-37139 Adelebsen (DE); Christian Viöl, Adelebsen (DE)

(73) Assignee: Wolfgang Viöl, Adelebsen (DE)

( * ) Notice: Subject to any disclaimer, the term of this patent is extended or adjusted under 35 U.S.C. 154(b) by 431 days.

(21) Appl. No.: 11/064,216

(22) Filed: Feb. 23, 2005

(65) Prior Publication Data

US 2005/0143775 A1 Jun. 30, 2005

Related U.S. Application Data

(63) Continuation-in-part of application No. PCT/EP03/09278, filed on Aug. 21, 2003.

(51) Int. Cl.
*A61N 1/00* (2006.01)

(52) U.S. Cl. .......................................................... 607/2

(58) Field of Classification Search ...................... 607/2
See application file for complete search history.

(56) References Cited

U.S. PATENT DOCUMENTS

| 4,667,677 | A | * | 5/1987 | Di Mino ....................... 607/71 |
| 4,846,179 | A | * | 7/1989 | O'Connor ..................... 607/72 |
| 6,383,183 | B1 | * | 5/2002 | Sekino et al. .................. 606/34 |
| 6,818,102 | B1 | * | 11/2004 | Viol ............................. 204/164 |

* cited by examiner

*Primary Examiner*—Mark Bockelman
(74) *Attorney, Agent, or Firm*—Thomas, Kayden, Horstemeyer & Risley LLP

(57) ABSTRACT

An apparatus for preparing a finger nail or a toe nail for a coating in that a gas discharge is ignited above the nail at atmospheric pressure comprises an electrode to be arranged above the nail, and a high voltage generator generating a high voltage to be applied to the electrode arranged above the nail for igniting the gas discharge between the electrode and the nail.

20 Claims, 1 Drawing Sheet

APPARATUS FOR PREPARING A FINGER NAIL OR A TOE NAIL FOR A COATING

CROSS REFERENCE TO RELATED APPLICATIONS

This application is a continuation in part of International Application PCT/EP03/09278 with an international filing date of Aug. 21, 2003 and claiming the benefit of co-pending German Patent Application No. 102 38 631.4 entitled "Verfahren und Vorrichtung zur Vorbereitung eines Finger-oder Fußnagels für eine Beschichtung, insbesondere eine Lackierung", filed on Aug. 24, 2002.

FIELD OF THE INVENTION

The invention relates to an apparatus for preparing a finger nail or a toe nail for a coating. Particular, the invention relates to an apparatus for preparing a fingernail or a toe nail with a coating of nail varnish.

BACKGROUND OF THE INVENTION

A preparation of a fingernail or a toe-nail for a coating, particularly for a coating with varnish, is necessary to provide for a sufficient wettening of the nail without using high amounts of the coating material on the one hand, and to provide for a long lasting coating on the other hand.

It is known to prepare a fingernail or a toe-nail for a coating in that the nail is cleaned and degreased with the aid of a liquid solvent. Nevertheless, a subsequently applied nail varnish often ships off within comparatively short time, after it has been cured. As a result, the remainders of the nail varnish have to be removed, and the step of lacquering has to be repeated, if an optically satisfying condition of the fingernail or toe-nail is to be maintained.

Thus, there is a demand for a new way of preparing a finger-nail or toe-nail for a coating, particularly with varnish, which makes it is possible to easily form a long lasting coating with little coating material, e.g. with small amounts of nail varnish.

SUMMARY OF THE INVENTION

The invention provides an apparatus for preparing a finger nail or a toe nail for a coating in that a gas discharge is ignited above the nail at atmospheric pressure, the apparatus comprising an electrode to be arranged above the nail, and a high voltage generator generating a high voltage to be applied to the electrode arranged above the nail for igniting the gas discharge between the electrode and the nail.

The use of so called corona or barrier discharges at atmospheric pressure is already known since some time for treating plastics, ceramics and the like to enhance their coating properties.

From U.S. Pat. No. 6,818,102 a corresponding method of modifying the surface of wood is known, in which the wood itself serves as a counter electrode for the gas discharge.

The preferred embodiments of the new apparatus for preparing a finger nail or a toe nail for a coating essentially operate quite similar to the known method of modifying wood surfaces. To ignite the gas discharge above the nail at atmospheric pressure, a high voltage is applied to the nail which acts between the electrode and the nail.

The gas discharge at atmospheric pressure modifies the surface of the nail in such a way that its surface energy is highly increased. This, for example, results in that a nail varnish which is applied onto the prepared nail easily spreads over the nail and strongly sticks to the nail. If the whole surface of the nail has modified by the gas discharge, then it will be observed, that a single drop of varnish locally applied to the nail fully spreads over the surface of the nail and covers the nail up to its edges without the necessity of manually spreading the varnish up to there.

Although the nail varnish sticks to a nail which has been pre-treated with the new apparatus much better than to a nail cleaned and degreased with the aid of a liquid solvent according to the prior art, the nail varnish may be removed from the nail with a usual nail varnish remover. The particular strong bond between nail varnish and a nail treated with the apparatus of the invention can also be exploited to use more environmental friendly nail varnishes, particularly nail varnishes with less or other solvents than used up to now, which do not result in satisfying lacquering results without the pre-treatment according to the invention.

The advantages of the invention are also useable for sticking false nails or other decorative objects to a nail and for achieving a better bond here than it has been possible according to the prior art.

Although a high voltage is applied between the electrode and the nail in igniting the gas discharge above the nail with the new apparatus, the currents flowing here are not dangerous, if it is cared for limiting these currents, which does not necessarily affect the results of the treatment of the nail.

To apply the high voltage between the electrode and the nail, an electric contact can be made to the skin of the finger or toe carrying the nail at a distance to the nail. This can be done to earthen the nail, particularly if the high voltage is generated with regard to earth. If the high voltage, however, is generated between two high-voltage outputs of the high voltage generator, one of these should be contacted with the electrode and the other of these should be contacted with the respective finger or toe.

With the new apparatus, the gas discharge is preferably ignited in air, i.e. in the gas, which forms the natural environment of the nail to be treated.

To limit the currents flowing between the electrode and the nail via the gas discharge, the gas discharge may be a dielectric barrier discharge. This means, a layer made of dielectric material is arranged between the electrode and the nail. Preferably, this layer of dielectric material is arranged directly in front of the electrode. A certain dielectric barrier results from the small electric conductivity of the horn material of the nail itself.

In a dielectric barrier discharge, it is essential that the high voltage which is applied between the nail and the electrode is an alternating high voltage. Even if the discharge is no dielectric barrier discharge, the high voltage can advantageously be an alternating high voltage as this inter alia limits the distances covered by the flowing loads driven by the high voltage.

An alternating high voltage in the frequency area of a few Hertz is preferred, because it can be generated particularly easily, for example by means of a piezo-generator.

A further measure to limit the currents flowing via the gas discharge is that the high voltage is a pulsed high voltage, i.e. consisting of high voltage pulses which are separated in time. If, further, a dielectric barrier is provided for the gas discharge, the pulses have to have alternating polarities.

In practice, it becomes evident that the distance between the electrode and the nail may not be too small for a good result of the coating pre-treatment. A distance of a few millimetres is preferred.

Advantageously, the electrode is arranged at a distance from 1 to 5 mm to the nail when igniting the gas discharge. Thus, the new apparatus may comprise a distance element defining a corresponding minimum distance between the electrode and the nail.

With a distance of 1 to 5 mm between the electrode and the nail, the necessary high voltage for igniting the gas discharge at atmospheric pressure is in the kV range.

Still a further measure to limit the current flowing via the gas discharge is to only ignite a gas discharge in a small volume, i.e. to only form a single discharge filament between the electrode and the nail. This discharge filament can then be used for modifying the entire surface of the nail by moving the electrode with regard to the nail. It is possible to work very precisely with the single discharge filament.

The electrode preferably has an electrode surface facing the nail and having a radius of curvature of less than 1 mm. This small radius of curvature of the electrode surface results in very high local field intensities even with limited, i.e. comparatively low, high voltages. Thus the gas discharge is ignited easily.

The distance element of the new apparatus is preferably made of an electrically isolating material to avoid short circuits via the distance element.

As already indicated before, the electrode is preferably moveable with regard to the nail. At the same time, the skin should be continuously contactable via the contact element which may be connected a second high voltage output of the high voltage generator.

It is to be noted that the gas discharge does not incur unpleasant stimulations or irritations. The noticeable stimulations of nerves in the finger or toe are much smaller than those which are experienced after static charging upon contact with a metallic object. This may be accounted to the comparatively low sensitivity of finger nails and toe nails. The current through the finger is little disturbing, so far as it is noticed at all.

An embodiment of the new apparatus which can be provided at particular low cost comprises a piezo-generator as the high voltage generator. Piezo-generators are widely used in gas lighters, for example. Such a Piezo-generator normally employed in a gas lighter can be used in the new apparatus. Thus, it is possible to produce the new apparatus based on known techniques at low cost.

BRIEF DESCRIPTION OF THE DRAWINGS

The invention can be better understood with reference to the following drawings. However, the components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
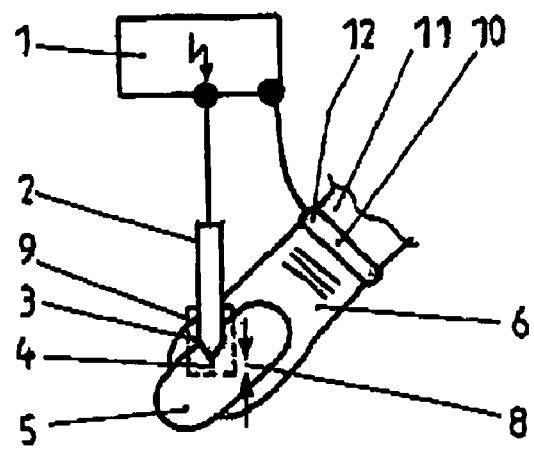
FIG. 1 shows a basic arrangement of a first preferred embodiment of the new apparatus in operation.

Referring now in greater detail to the drawings, FIG. 1 illustrates a finger nail 5 of a finger 6 of a hand (not fully depicted here) together with an apparatus for pre-treating the nail 5 for a subsequent lacquering with nail varnish. The apparatus comprises an electrode 2 having a pointed electrode tip 3 which is arranged above the finger nail 5. The electrode tip 3 keeps a distance 8 to the nail 5, which is determined by a distance element 9 which is not fully depicted here but indicated with a dashed line. The electrode 2 is connected to one of two high voltage outputs of a high voltage generator 1. The other high voltage output is connected to a contact element 10 which in turn contacts the skin 11 of the finger 6 at a distance to the nail 5. The contact element 10 is formed as a contact ring 12 here, which contacts the skin 11 over a large contact area, thus reducing the current densities occurring across the skin 11. The high voltage generator 1 generates a high voltage in the kV-range which is applied between the electrode 2 and—via the contact element 10—the nail 5 produces a gas discharge 4 between the electrode tip 3 and the nail 5. The gas discharge 4 occurs in form of a localized discharge filament and modifies the surface of the nail 5 so that its surface energy is essentially increased. This makes a subsequent coating of the finger-nail 5, for example with a nail varnish, very easy, because the nail varnish very easily spreads over the entire pre-treated surface of the nail 5. Further, the varnish much better bonds to the nail 5. To modify the entire surface of the nail 5, it is necessary to scan the entire surface of the nail 5 with the discharge filament extending from the electrode tip 3 by moving the electrode 2 with regard to the nail 5.

Figure 2:
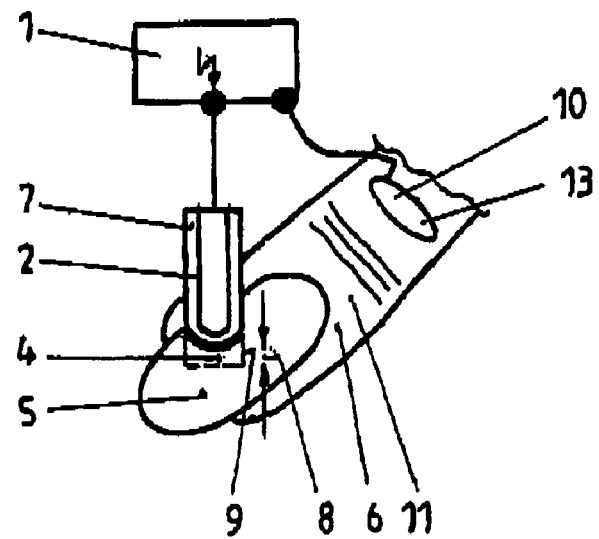
FIG. 2 shows a basic arrangement of a second preferred embodiment of the new apparatus in operation.

The embodiment of the apparatus of the invention illustrated in FIG. 2 differs from that one shown in FIG. 1 in that the electrode 2 is shielded by a dielectric layer 7 so that the gas discharge 4 is a dielectric barrier discharge. Thus, the current which flows through the gas discharge 4 and the finger 6 is strongly limited. The current can further be limited (as in the embodiment according to FIG. 1) in that the high voltage generator 1 generates single high voltage pulses at a distance in time. For maintaining the dielectric barrier these separate high voltage pulses have to have alternating polarities. Under these condition dangerous current densities through the finger 6 can definitively be avoided. The distance element 9 can be made of the same material at the dielectric layer 7. It preferably anyway consists of a not electrically conductive material. The contact element 10 according to FIG. 2 is no contact ring but a small contact pad 13. In every case, the contact to the skin 11 of the finger 6 even at a distance to the finger nail 5 has the effect that the finger nail 5 acts as a counter electrode for the gas discharge 4 above the nail 5. With a dielectric barrier discharge, the nail 5 even then acts as a counter electrode, when the high voltage generator 1 is only contacted to the electrode 2 because of the capacitance of the nail 5. The gas discharge 4 takes place under atmospheric pressure, and normally in simple air. To the air, however, certain gases may be added, which may effect a further modification of the surface of the nail 5, if desired.

The modification of the nail 5 by means of one of the apparatus of the invention illustrated in FIGS. 1 and 2 is given for some minutes so that at first all nails of the fingers of one hand may be pre-treated and then be coated with nail varnish, for example. All ten finger nails or all ten toe nails may also be pre-treated first, before lacquering is started.

Many variations and modifications may be made to the preferred embodiments of the invention without departing substantially from the spirit and principles of the invention. All such modifications and variations are intended to be included herein within the scope of the present invention, as defined by the following claims.

LIST OF REFERENCE NUMERALS 1 high voltage generator
2 electrode
3 electrode tip 4 gas discharge
5 nail
6 finger
7 dielectric layer
8 distance
9 distance element
10 contact element
11 skin
12 contact ring
13 contact pad

We claim:

1. A method for preparing a finger nail or a toe nail for a coating wherein a gas discharge is ignited above the nail at atmospheric pressure, the method comprising:
   arranging an electrode above the nail, wherein the electrode is covered with a dielectric barrier so that the gas discharge is a dielectric barrier discharge;
   generating with a high voltage generator a high voltage to be applied to the electrode arranged above the nail for igniting the gas discharge between the electrode and the nail; and
   coating the nail pre-treated by the dielectric barrier discharge.

2. The method of claim 1, wherein the high voltage generator comprises two output terminals between which the high voltage is generated, one of these two output terminals being connected to the electrode.

3. The method of claim 2, wherein the other of the two output terminals being connected to earth.

4. The method of claim 2, wherein the other of the two output terminals being connected to a contact element for electrically contacting a skin of a hand or a foot carrying the nail at a distance to the nail.

5. The method of claim 4, wherein the contact element is a contact ring.

6. The method of claim 1, wherein the dielectric barrier covering the electrode comprises an outer surface adapted to face the nail and having a radius of curvature smaller than 1 mm.

7. The method of claim 1, wherein the high voltage generator generates the high voltage as separated alternating high voltage pulses.

8. The method of claim 7, wherein the high voltage generator generates the high voltage pulses at a frequency in a range of 1 to 10 Hz.

9. The method of claim 7, wherein the high voltage generator is a piezo-generator.

10. The method of claim 1, wherein the high voltage generator generates the high voltage in a range of 1 to 100 kV.

11. The method of claim 1, and further comprising defining minimum distance between the electrode and the nail using a distance element.

12. The method of claim 11, wherein the minimum distance is in a range of 1 to 5 mm.

13. The method of claim 11, wherein the distance element is made of an electrically isolating material.

14. The method of claim 1, wherein the electrode comprises a electrode surface adapted to face the nail and having a radius of curvature smaller than 1 mm.

15. A method for pre-treating a finger nail or a toe nail for a coating, the method comprising:
   arranging an electrode above the nail for a coating;
   generating a high voltage with a high voltage generator;
   applying the high voltage to the electrode arranged above the nail to ignite a gas discharge between the electrode and the nail, wherein the electrode is covered with a dielectric barrier so that the gas discharge is a dielectric barrier discharge; and
   coating the nail pre-treated by the dielectric barrier discharge.

16. A kit for preparing a finger nail or a toe nail for a coating wherein a gas discharge is ignited above the nail at atmospheric pressure, the apparatus comprising:
   an electrode to be arranged above the nail;
   a high voltage generator generating a high voltage to be applied to the electrode arranged above the nail for igniting the gas discharge between the electrode and the nail, wherein the electrode is covered with a dielectric barrier so that the gas discharge is a dielectric barrier discharge, wherein the high voltage generator generates the high voltage as separated alternating high voltage pulses; and
   nail varnish to be applied to the pre-treated nail.

17. The kit of claim 16, wherein the high voltage generator generates the high voltage pulses at a frequency in a range of 1 to 10 Hz.

18. The kit of claim 17, wherein the high voltage generator is a piezo-generator.

19. The kit of claim 18, wherein the high voltage generator generates the high voltage in a range of 1 to 100 kV.

20. The kit of claim 16, wherein the dielectric barrier covering the electrode comprises an outer surface adapted to face the nail and having a radius of curvature smaller than 1 mm.

* * * * *